United States Patent [19]
Moses

[11] Patent Number: 5,882,928
[45] Date of Patent: Mar. 16, 1999

[54] IN VITRO MATURATION AND FERTILIZATION OF MAMMALIAN OOCYTES

[75] Inventor: Ruth Miriam Moses, Toronto, Canada

[73] Assignee: Oocytechs Research Corporation, Toronto, Canada

[21] Appl. No.: 824,921

[22] Filed: Mar. 27, 1997

[51] Int. Cl.$^6$ .................. C12N 5/00; A01N 1/02
[52] U.S. Cl. ............ 435/375; 435/1.1; 435/1.3; 435/366; 435/377
[58] Field of Search .............. 435/1.1, 1.3, 366, 435/375, 377

[56] References Cited

PUBLICATIONS

Tornell et al., "Effect of cyclic AMP on the isolated human oocyte–cumulus complex", Human Reproduction 8 (5) : 737–739 (1993).
Son et al., "Effects of 1,2–propanediol and freezing–thawing on the in vitro developmental capacity of human immature oocytes", Fertility and Sterility 66 (6) : 995–999 (1996).
Petr et al., "Effect of Testosterone and dibutyryl c–AMP on the meiotic competence in pig oocytes of various size catagories" Theriogenology 46 : 97–108 (1996).
Cha et al., "Pregnancy after in vitro fertilization of human follicular oocytes collected from nonstimulated cycles, their culture in vitro and their transfer in a donor ooocyte program", Fertility and Sterility 55 (1) : 109–13 (1991).
Schroeder, A.C. & Eppig, J.J., Dev. Biol. 102: 493–497 (1984).
Cho, W.K., Stern, S. & Biggers, J.D., J. Exp. Zool. 187: 383–386 (1974).

*Primary Examiner*—Sandra E. Saucier
*Attorney, Agent, or Firm*—Bell, Boyd & Lloyd

[57] ABSTRACT

An in vitro fertilization method comprising culturing mammalian immature oocytes obtained from a mammalian ovary very early in the mammal's menstrual cycle in an oocyte maturation inhibitor-containing culture, removing the inhibitor and maturing and fertilizing the oocytes to produce embryos for subsequent uterine-implantation. The method allows for more convenient, efficacious, safer, less expensive and timely implantation of a plurality of embryos in the uterus to enhance pregnancy success rate. Cryopreservation of the immature oocytes offers enhanced benefits Preferably, the mammal is human and the inhibitor is dbcAMP.

5 Claims, No Drawings

IN VITRO MATURATION AND FERTILIZATION OF MAMMALIAN OOCYTES

FIELD OF THE INVENTION

This invention relates to in vitro maturation and fertilization of mammalian oocytes, particularly, human oocytes, and to aqueous nutrient solutions containing said oocytes.

BACKGROUND TO THE INVENTION

In vitro fertilization (IVF) of human oocytes is a widely practiced medical technique used to overcome various forms of female and male infertility. As a result of this procedure, tens of thousands of babies have been born world-wide to previously infertile couples. Although first practised to treat women with blocked Fallopian tubes, IVF has been successfully applied to treat other types of infertility. However, one application that has not been found to be possible is IVF using cryopreserved immature oocytes.

Cryopreservation of sperm is a well-established technique which allows the preservation of fertility for men who have medical conditions which will result in the loss of their ability to produce healthy, functional sperm. The availability of cryopreserved sperm also greatly facilitates the availability of sperm from anonymous donors to be used for therapeutic donor insemination. However, such possibilities are not available for women who are about to lose their fertility, or who require donor oocytes because very few unfertilized oocytes have been successfully cryopreserved and subsequently fertilized (reviewed by Bernard and Fuller, *Human Reprod. Update* 2: 193–207, 1996; Chen, *Lancet* i: 884–886, Apr. 19, 1986; van Uem et al.,*Lancet* i: 752–753, Mar. 28, 1987). This problem is unique to unfertilized oocytes, since fertilized oocytes and embryos are routinely successfully cryopreserved for future use.

The ovaries of most women in the childbearing years contain thousands of immature oocytes. However, immature oocytes cannot be fertilized until they have undergone maturation. In each menstrual cycle, usually only one oocyte matures to be released from the ovary at the time of ovulation, and possibly fertilized. When IVF was first performed, the one mature unfertilized oocyte was removed from the ovary just prior to ovulation. It was fertilized in a laboratory dish (in vitro) and the resulting embryo was transferred back to the woman's uterus. However, it was found that if more oocytes were available for fertilization, there were more embryos available for transfer to the uterus and this significantly increased the pregnancy rate. Therefore, the current clinical practice involves giving patients hormone injections in order to induce the maturation of approximately twenty oocytes. Just prior to ovulation, the mature oocytes are removed from the ovaries using an ultrasonographically guided probe inserted in the vagina. The oocytes are then placed in appropriate culture medium and mixed with either partner or donor sperm. After twenty-four hours, the oocytes are evaluated for signs of fertilization and fertilized oocytes are kept in culture for 2 to 5 more days, to allow them to develop into embryos. Generally, up to 3 embryos are transferred to the woman's uterus. Any additional embryos may be cryopreserved for future use (Wood, C. and Trounson, A. eds "Clinical in Vitro Fertilization" Berlin: Springer-Verlag 1989).

The administration of hormone injections to induce the maturation of many oocytes simultaneously is known as controlled ovarian hyperstimulation (COH). The advantage of COH is the availability of many more mature oocytes for fertilization, which increases the chances of pregnancy. However, it is necessary that the effects of the injections are closely monitored by daily ultrasound examinations of the ovaries and blood hormone measurements, since excessive ovarian stimulation may cause ovarian hyperstimulation syndrome (OHSS), which is a serious and potentially fatal condition.

Some disadvantages of COH are listed as follows:

1. The risk of OHSS.
2. The requirement for twice daily hormone injections and daily ultrasound examinations and blood tests. Each of these requirements is inconvenient, uncomfortable and expensive.
3. The timing of oocyte retrievals and fertilization is determined by the patient's response to COH. Accordingly, patients and health care providers must be available seven days a week.
4. Some patients fail to produce an adequate number of oocytes, despite the administration of large amounts of hormones.

An alternative way of obtaining mature oocytes for IVF is to remove immature oocytes from the ovaries and to allow them to mature in vitro. Mammalian oocytes, including human oocytes, are known to undergo maturation in vitro. In the case of mice, cattle and other mammals, in vitro matured oocytes have been fertilized in vitro and given rise to normal healthy offspring when embryos were transferred to an appropriate uterus (Schroeder and Eppig 1984 Dev. Biol. 102:493; Sirar et al. 1988, Biol.Reprod. 39:546). A few similar attempts have been carried out in humans, resulting in pregnancies in approximately 2% of patients treated (Cha et al., 1991, Fertil. Steril. 55:109; Trounson et al., 1994, Fertil. Steril. 62:353; Barnes et al., Hum. Reprod. 1995, 10:101; Russell et al., 1996, Human Reprod. 11: Abstract Book 1, p.2).

Mammalian oocytes, including human oocytes, undergo spontaneous maturation in vitro when removed from the ovaries and cultured under physiological conditions, with human immature oocytes becoming mature within 48 hours. Previous investigators have removed oocytes from the ovaries 3–8 days prior to the expected time of ovulation, allowed the oocytes to mature in vitro for 48 hours, fertilized them, and approximately 48 hours after fertilization, transferred the resulting embryos to the uterus. However, the timing of fertilization and embryo transfer are generally not optimal for the following reasons.

1. Oocyte quality

Ovaries contain thousands of immature oocytes. In any given month, early in the menstrual cycle, several oocytes begin to grown in preparation for undergoing maturation and becoming developmentally competent, i.e. competent to be fertilized and develop into a healthy mammal. By approximately the fifth to seventh day of the cycle, one oocyte becomes dominant and continues to grow while the others are induced to degenerate. Once an oocyte becomes dominant, it grows and undergoes metabolic changes for approximately one week prior to becoming mature at the time of ovulation. Oocytes that do not undergo this growth phase will mature in vitro and can be fertilized, but are less likely to be developmentally competent. Therefore, the optimal time to obtain the largest number of immature oocytes is early in the cycle before any oocytes have begun to degenerate. However, unfortunately, oocytes removed early in the menstrual cycle and matured in vitro, are less likely to be developmentally competent.

2. Timing of Embryo Transfer

When immature oocytes are obtained early in the menstrual cycle and allowed to mature, they are fertilized earlier in the cycle than would normally occur. This results in the formation of embryos which are then placed in the uterus at a time in the menstrual cycle which is earlier than that which would occur as a result of fertilization in a natural cycle. The endometrium, the lining of the uterus, undergoes growth and development during the menstrual cycle, in preparation for embryo implantation. If the embryo arrives in the uterus too early, the endometrium is not adequately developed, and implantation cannot occur. This problem has been addressed by preparing the endometrium to be ready sooner by the administration of hormones. However, this approach may not provide the optimal conditions for embryo implantation.

One solution to these problems would be to delay fertilization of mature oocytes until a more physiological time in the menstrual cycle. However, mature eggs that are kept in culture for more than 24 hours begin to deteriorate and after 48 hours can no longer be fertilized.

Another solution is to maintain oocytes in culture in the immature state. In the ovary, oocytes remain in the immature state until stimulated to mature by the hormone, luteinizing hormone (LH). Therefore, it seems that there is an inhibitor in the ovary which prevents the premature maturation of oocytes which occurs spontaneously in vitro. This inhibitor has been named oocyte maturation inhibitor (OMI) but its molecular nature has not yet been identified, despite more than 20 years of research. However, it is known that compounds which increase the levels of oocyte cyclic adenosine monophosphate (cAMP), a ubiquitous intracellular signalling molecule, prevent oocyte maturation in vitro (Cho et al., 1974, J. Exp. Zool. 187:383). Accordingly, including a compound which increases levels of oocyte cAMP in the culture medium, allowed immature oocytes from immature mice to grow in vitro to a size at which they were developmentally competent (Chesnel et al., 1994, Dev. Biol., 161:285).

The technical ability to successfully and controllaby mature oocytes in vitro has a direct application to the problem of mature oocyte cryopreservation. To-date, attempts at oocyte cryopreservation have involved the use of mature oocytes, since these are the oocytes that can be successfully fertilized in vitro. However, mature oocytes do not survive cryopreservation well because mature oocytes are at the metaphase stage of the cell cycle wherein they contain a microtubule spindle along which the paired chromosomes are arranged. At the time of fertilization, the chromosomes separate, one member of each pair travelling in opposite directions along tracks provided by the spindle fibres. Any disruption of the spindle can lead to incorrect chromosome separation, which is severely detrimental or lethal to a cell. Freezing is known to cause the disappearance of the spindle and disruption of the chromosome arrangement. The spindle reforms upon thawing, but the chromosomes may no longer be correctly arranged. Disruption of the spindle impairs cleavage divisions, which are essential to normal embryonic development. The disruption of the spindle caused by cryopreservation may well explain the poor results seen with cryopreserved oocytes. In contrast, immature oocytes, at the prophase stage of the cell cycle, do not contain a microtubule spindle. Therefore, the cryopreservation of immature oocytes eliminates the problem of damage to the spindle. However, if immature oocytes are to be cryopreserved, it is necessary to have a technique whereby after thawing they can be successfully and controllably matured and fertilized in vitro.

However, to-date, there remains a need for a clinical IVF procedure which is more convenient, less potentially harmful and less expensive for mammals, particularly humans. The present invention provides such a technique.

SUMMARY OF THE INVENTION

The invention describes a new technique for the maturation of human oocytes in vitro, which greatly improves the success of the pregnancy as compared to that reported in the prior art.

It is an object of the present invention to provide an improved method of clinical IVF which method is more convenient, less expensive and less harmful for mammals.

It is a further object of the present invention to provide said IVF method which uses cryopreserved immature unfertilized oocytes.

Thus, one essential step in the in vitro maturation procedure according to one embodiment of the present invention is the use of dibutyryl cAMP (dbcAMP), which reversibly increases oocyte cAMP levels in the medium used to culture immature oocytes when they are first removed from the ovaries at a very early stage of development. This allows the oocytes to grow in culture as they would do in vivo. At the appropriate time in the menstrual cycle, the oocytes are transferred to dbcAMP-free medium, where they undergo maturation in preparation for being fertilized and subsequently transferred to the uterus.

Accordingly, in one aspect the invention provides an IVF method comprising a method of culturing immature mammalian oocytes from a first stage of development to a second stage of development in a suitable culture medium in vitro, without maturation of said oocytes, wherein said culture medium contains an effective amount of oocyte maturation inhibitor.

Preferably, the oocyte maturation inhibitor is dbcAMP. Other oocytes maturation inhibitors (Chesnel et al, 1994, Dev.Biol., 161:285) may be used.

The preferred method is set out, generally, as follows.

1. At a time between day 3 and day 5 of the menstrual cycle, ovarian follicles from 2 to 10 mm in diameter are identified using transvaginal ultrasonography and by use of a transvaginal probe, oocytes are aspirated from these follicles into a physiologically acceptable culture medium containing an effective concentration of dbcAMP to inhibit maturation.
2. The immature oocytes are cultured for 5 to 7 days which allows them to grow and develop to be subsequently developmentally competent, without undergoing maturation.
3. The oocytes are then rinsed in, and transferred to, a physiologically acceptable culture medium free of dbcAMP and allowed to mature.
4. Forty-eight hours later, the oocytes are examined and those which are mature are transferred to culture dishes containing the selected and desired sperm. After 4 hours, oocytes are transferred to fresh culture medium.
5. The next day, oocytes are examined for signs of fertilization. Fertilized oocytes are monitored as they undergo embryonic development.
6. Generally, one to three embryos are transferred to a uterus between 2 and 5 days after fertilization.
7. Any additional embryos may be cryopreserved for future use, as is standard practice.

In a further aspect, the invention provides a method of preparing a mature mammalian oocyte for subsequent fertilization comprising preparing said immature oocyte at said second stage of development by a method as hereinabove defined further comprising removing said culture medium containing said oocyte maturation inhibitor from said immature oocyte, and culturing said immature oocyte in an oocyte maturation inhibitor—free culture medium to produce said mature oocyte.

In a yet further aspect, the invention provides fertilizing said mature oocytes as hereinbefore prepared with suitable sperm.

In a still yet further aspect the invention provides a method of enhancing the acceptance rate for embryo development in the uterus of said mammal, said method comprising culturing a plurality of said fertilized oocytes prepared as hereinbefore defined to provide a plurality of embryos and transplanting all or some of said embryos in said uterus.

In a further aspect the invention provides methods as hereinbefore defined comprising the cryopreservation of said immature oocytes.

The invention further provides a solution for the culture of immature human oocytes, said solution comprising an effective oocyte maturation inhibitive amount of an oocyte maturation inhibitor.

The invention further provides a culture solution comprising immature mammalian oocytes, 5–8 days after removal from the ovary of said mammal, said oocytes having been obtained from said mammalian ovary at day 3 to day 5 of the menstrual (hormonal) cycle, for use in IVF.

The invention further provides a mature mammalian oocyte obtained by the maturation of said 5–8 day old oocyte as hereinabove defined.

The invention further provides a solution as hereinabove defined wherein said oocyte maturation inhibitor is dbcAMP.

For patients who are concerned about future loss of fertility, but who do not wish to have IVF at this time, immature oocytes are removed as described hereinabove and then cryopreserved using a method similar to that described by Son et al. (1996, Fertil. Steril., 66:995). This involves a one-step freezing method using, generally, propanediol as the cryoprotectant.

When patients wish to have IVF, oocytes are thawed, and then cultured, first in medium containing dbcAMP, as described hereinabove. After 5 to 7 days, the immature oocytes are transferred to dbcAMP-free medium and allowed to mature for 2 days prior to IVF. Resulting embryos are transferred to the uterus 2 to 5 days after fertilization.

Thus, the essence of the present invention is to utilize immature oocytes obtained very early in the mammal's hormonal cycle to subsequently obtain sufficient numbers of mature oocytes at the most desirable time for fertilization and implantation into the uterus while not having the aforesaid prior art disadvantages, to provide a clinical IVF procedure which is more convenient, less potentially harmful and less expensive for mammals and patients.

DESCRIPTION OF PREFERRED EMBODIMENTS

In order that the invention may be better understood, preferred embodiments will now be described by way of example only.

Experiment

A. In Vitro Oocyte Maturation

1. Between day 3 and day 5 of the menstrual cycle, ovarian follicles from 2 to 10 mm in diameter are identified using transvaginal ultrasonography. Using a transvaginal probe, oocytes are aspirated from these follicles into Nutrient Ham F-10 Mixture with 20 mM Hepes, without sodium bicarbonate and L-gluatamine (Sigma Chemical Co., St. Louis, MO), supplemented with 75 mg/l penicillin G, 50 mg/l streptomycin sulfate, 20% patient's serum and 200 ug/ml dbcAMP.

2. The aspirate obtained is transferred to petri dishes (Falcon 1002) and examined under a dissecting microscope which has a stage heated to 37° C. Immature oocytes with attached cumulus cells are identified, rinsed in and transferred to double-welled culture dishes (Falcon 3037) containing 0.5 ml. Medium 199 with Earle's salts, L-glutamine and sodium bicarbonate (Sigma) supplemented with 0.23 mM pyruvic acid, 31.3 mM sodium lactate, 0.05 mM disodium ethylenediaminetetraacetic acid, 75 mg/l penicillin G, 50 mg/l streptomycin sulfate, 200 ug/ml dbcAMP (Chesnel et al., 1994, Dev. Biol. 161:285) and 20% patient's serum. Oocytes are cultured for 5 to 7 days at 37° C. in an atmosphere of 5% $CO_2$, 5% $O_2$ and 90% $N_2$, allowing them to grow and develop without undergoing maturation.

3. The oocytes are then rinsed in, and transferred to, M199 modified as above but free of dbcAMP, and allowed to mature.

4. Two days later, the oocytes are examined under the dissecting microscope. Those which have emitted the first polar body and are, therefore, mature are transferred to culture dishes containing Ham's F-10 medium supplemented with 20% patient's serum and containing $1 \times ^{104}$ sperm/ml of the patient's choice. After 4 hours, oocytes are transferred to fresh Ham's F-10.

5. The next day, oocytes are examined for signs of fertilization. Fertilized oocytes are transferred to culture dishes containing CZB medium (Chatot et al., 1985, J. Reprod. Fertil. 86:679; FitzGerald and DiMattina, 1992, Fertil. Steril. 57:64) and embryonic development is monitored daily.

6. One to three embryos are transferred to the patient's uterus between 2 and 5 days after fertilization.

7. Any additional embryos are cryopreserved for future use, as is standard practice.

B. Patient Preparation for Embryo Transfer

Patients who have had oocytes retrieved have transvaginal ultrasound examinations of the endometrium every three to four days to ensure that the endometrium is developing well in preparation for embryo implantation.

a) Patients who have ovulatory cycles and normal endometrial development have serum estradiol, LH and progesterone measured on the day that the oocytes are allowed to mature. Patients who have not had an endogenous LH surge are given 10,000 I.U. human chorionic gonadotrophin by injection. All patients begin using 200 mg progesterone vaginal suppositories twice a day on the day of fertilization.

b) Patients who are known to be anovulatory, or who are known to have poor endometrial development take 4 mg 17-B estradiol daily from the day of oocyte retrieval. This is increased as necessary according to endometrial development as assessed by ultrasonography. Patients begin using 200 mg progesterone vaginal suppositories twice daily from the day of fertilization.

C. Cryopreservation of Immature Oocytes

When patients wish to have IVF, oocytes are thawed using a method similar to that described by Son et al. (1996, Fertil. Steril., 66:995), and then cultured as described above, first in medium containing dbcAMP. After 5 to 7 days, they are transferred to dbcAMP free medium and allowed to mature for 2 days prior to IVF. Resulting embryos are transferred to the patient's uterus 2 to 5 days after fertilization, as described above.

The present invention may also be enhanced by using the intracytoplasmic sperm injection (ICSI) technique, wherein a sperm microinjected directly into the egg, eliminating the requirement for sperm penetration of the egg in order for fertilization to occur. ICSI is a well established technique, first described by Palermo et al. (1992 Lancet; 340:17), used where few sperm are available for IVF. Russell et al. (1996 Human Reprod. 11: Abstract Book 1, p. 2) used ICSI when he achieved the pregnancy using in vitro matured oocytes.

Results

The use of the in vitro matured oocytes as hereinbefore prepared results in a pregnancy rate similar to that seen with IVF as it is currently practiced.

It can be readily seen that some of the advantages of the present invention are as follows:

1. The administration of hormone injections is avoided. This makes the clinical IVF procedure of the invention safer, more convenient and less expensive and thus makes IVF possible for more infertile couples.
2. The timing of oocyte retrieval is more flexible. This makes the invention procedure more convenient and less expensive since health care providers do not have to be available seven days a week.
3. The availability of immature oocyte cryopreservation makes it possible to preserve the fertility of women who are about to lose their fertility.
4. The availability of immature oocyte cryopreservation facilitates oocyte donation.
5. That the clinical IVF procedure of this invention is now safer, more convenient and less expensive then prior art techniques will probably result in the availability of more donor oocytes for women who do not have their own functional oocytes.

Although this disclosure has described and illustrated certain preferred embodiments of the invention, it is to be understood that the invention is not restricted to those particular embodiments. Rather the invention includes all embodiments which are functional or mechanical equivalence of the specific embodiments and features that have been described and illustrated.

I claim:

1. A method for in vitro fertilization of human oocytes from a sexually mature female comprising the steps of:
    a) obtaining immature oocytes at a first stage of prophase development wherein no in vitro incubation has taken place,
    b) directly incubating said immature oocytes in a medium wherein the medium consists essentially of an oocyte maturation inhibitor which increases levels of cyclic adenosine monophosphate in the oocytes and a culture medium, wherein a second stage of prophase development occurs after incubation with said maturation inhibitor,
    c) incubating said immature oocytes in a medium without said oocyte maturation inhibitor, wherein mature oocytes are produced,
    d) fertilizing in vitro said mature oocytes with sperm to produce at least one fertilized oocyte,
    e) culturing said fertilized oocyte to produce an embryo, and
    f) transferring at least one embryo to the uterus of a human.

2. The method of claim 1, wherein said oocyte maturation inhibitor is dibutyryl cyclic adenosine monophosphate.

3. The method of claim 1, wherein said immature oocytes at said second stage of development are developmentally competent.

4. The method of claim 1, wherein said immature oocytes are cultured for 5–7 days in the medium consisting essentially of an oocyte maturation inhibitor which increases levels of cyclic adenosine monophosphate in the oocytes and a culture medium to said second stage of development.

5. The method of claim 1, further comprising:
    i) cryopreserving said immature oocytes at said first stage of development and
    ii) thawing said cryopreserved immature oocytes prior to culturing said immature oocytes in the medium consisting essentially of an oocyte maturation inhibitor which increases levels of cyclic adenosine monophosphate in the oocytes and a culture medium.

* * * * *